US010739300B2

(12) United States Patent
Ujihara et al.

(10) Patent No.: US 10,739,300 B2
(45) Date of Patent: Aug. 11, 2020

(54) SENSOR ELEMENT

(71) Applicant: NGK INSULATORS, LTD., Nagoya (JP)

(72) Inventors: Kosuke Ujihara, Tokai (JP); Toru Hayase, Nagoya (JP); Kenji Morimoto, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 239 days.

(21) Appl. No.: 15/915,514

(22) Filed: Mar. 8, 2018

(65) Prior Publication Data

US 2018/0284050 A1    Oct. 4, 2018

(30) Foreign Application Priority Data

Mar. 31, 2017  (JP) ................... 2017-072046
Mar. 31, 2017  (JP) ................... 2017-072226
May 10, 2017   (JP) ................... 2017-093728

(51) Int. Cl.
*G01N 27/406* (2006.01)
*G01N 33/00* (2006.01)
*G01N 27/417* (2006.01)
*G01N 27/407* (2006.01)

(52) U.S. Cl.
CPC ..... *G01N 27/4067* (2013.01); *G01N 27/4071* (2013.01); *G01N 27/417* (2013.01); *G01N 33/0027* (2013.01)

(58) Field of Classification Search
CPC .......... G01N 27/4067; G01N 27/4071; G01N 27/417; G01N 33/0027
See application file for complete search history.

(56) References Cited

U.S. PATENT DOCUMENTS

| 2001/0008211 A1* | 7/2001 | Kato ............... G01N 27/4074 204/426 |
| 2004/0031786 A1* | 2/2004 | Heimann .......... G01N 27/4067 219/543 |
| 2006/0091008 A1* | 5/2006 | Heimann .......... G01N 27/4067 204/408 |

FOREIGN PATENT DOCUMENTS

| JP | 3096281 B2 | 8/2000 |
| JP | 3668050 B2 | 7/2005 |
| JP | 3873302 B2 | 1/2007 |

(Continued)

OTHER PUBLICATIONS

U.S. Appl. No. 15/915,467, filed Mar. 8, 2018, Kosuke Ujihara et al.
(Continued)

*Primary Examiner* — Paul M. West
(74) *Attorney, Agent, or Firm* — Burr & Brown, PLLC

(57) ABSTRACT

A heater part of a planar sensor element includes: a Pt heater element; and an insulating layer including 90-99.9 wt % of an insulating material having a different coefficient of thermal expansion from a solid electrolyte forming a base part of the element. The heater part other than a heater electrode is buried in the base part. The heater element has a thickness of 10-50 μm and is covered with the insulating layer. The insulating layer has a porosity of 4% or less and a thickness of 50-150 μm. The distances of the insulating layer from an end portion of the element, from a main surface on which the heater electrode is located, and from a side surface of the element are respectively 0.25-0.75 mm, 0.20-0.60 mm, and 0.20-0.60 mm. The total length of the element is 80.0 mm or less.

7 Claims, 4 Drawing Sheets

(56) References Cited

FOREIGN PATENT DOCUMENTS

| | | | |
|---|---|---|---|
| JP | 4573939 | B2 | 11/2010 |
| JP | 4980996 | B2 | 7/2012 |

OTHER PUBLICATIONS

U.S. Appl. No. 15/915,536, filed Mar. 8, 2018, Kosuke Ujihara et al.

* cited by examiner

F I G. 5
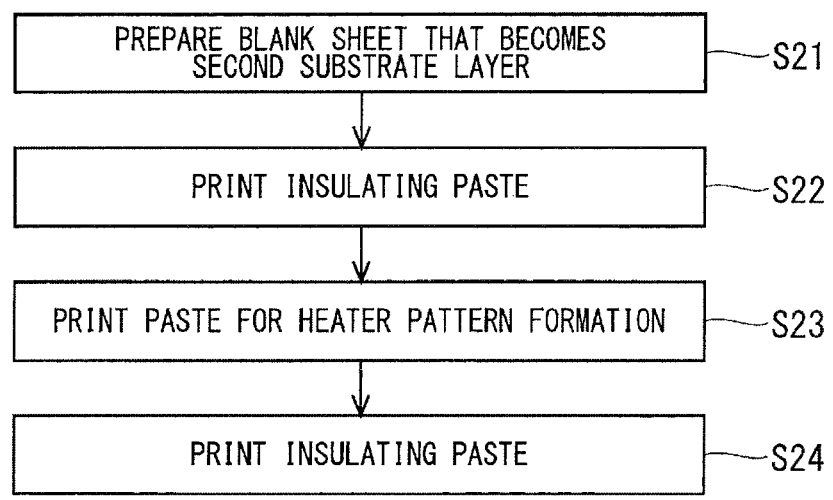

SENSOR ELEMENT

BACKGROUND OF THE INVENTION

Field of the Invention

The present invention relates to a sensor element formed of an oxygen-ion conductive solid electrolyte, and, in particular, to the configuration of a heater included in the sensor element.

Description of the Background Art

As an apparatus for measuring the concentration of a predetermined gas component (e.g., $O_2$, NOx, HC, and CO) in a measurement gas, including a combustion gas and an exhaust gas in an internal combustion engine, such as an engine of a vehicle, a gas sensor including a sensor element formed of an oxygen-ion conductive solid electrolyte, such as zirconia ($ZrO_2$), has been known.

As such a sensor element of the gas sensor (gas sensor element), a sensor element having a structure in which a sensor part for performing detection of a target gas component and the like and a heater part including a heater for heating the sensor part to activate the oxygen-ion conductive solid electrolyte forming the sensor part are laminated and integrated is widely known. The sensor element having this structure has the advantage of being able to quickly heat the sensor element (sensor part) to a desired driving temperature (or activation temperature) at the start of driving of the gas sensor.

Such a heater usually includes a heater element including a resistive heating part formed of metal, such as Pt (platinum), and an insulating layer surrounding the heater element to electrically insulate the heater element from the surroundings. Alumina, spinel, or the like is used as an insulating material for the insulating layer.

When such a sensor element is used continuously, a temperature cycle including heating during use and cooling after use is repeated, and, each time the temperature cycle is repeated, stress is caused on the insulating layer by a difference in coefficient of thermal expansion between the insulating layer and solid electrolyte layers surrounding the insulating layer. A sensor element in which the insulating layer has a porous structure to prevent or reduce the occurrence of cracking in the insulating layer caused by the action of the stress is already known (see, for example, Japanese Patent No. 3668050).

A sensor element in which the coefficient of thermal expansion (thermal expansion rate) of the solid electrolyte layers or the insulating layer has been adjusted to relax the stress caused due to the difference in thermal expansion is also already known (see, for example, Japanese Patent No. 3873302 and Japanese Patent No. 4980996). Japanese Patent No. 3873302 discloses an embodiment of adjusting the coefficient of thermal expansion of the solid electrolyte layers by causing zirconia forming the solid electrolyte layers to be in mixed phase of C phase (cubic phase) and M phase (monoclinic phase). On the other hand, Japanese Patent No. 4980996 discloses an embodiment of adjusting the coefficient of thermal expansion of the insulating layer by adding a rare-earth element to alumina forming the insulating layer, so that the coefficient of thermal expansion of the insulating layer is equal to the coefficient of thermal expansion of the solid electrolyte layers.

Furthermore, a sensor element in which only an interface portion of the insulating layer with the solid electrolyte layers being in contact with the insulating layer has been densified to ensure adhesion of the solid electrolyte layers to the insulating layer is already known (see, for example, Japanese Patent No. 3096281).

In addition, a cylindrical sensor element in which reduction in thermal shock resistance is prevented or reduced while including a dense insulating layer is already known (see, for example, Japanese Patent No. 4573939).

The driving temperature (heating temperature to which the sensor element is heated by the heater) when the sensor element is driven may be determined appropriately in accordance with the configuration of the sensor element, a material for each component, performance requirements for the sensor element, and the like. However, in the case that a conventional sensor element including a heater that includes a heater element formed of Pt and a porous insulating layer is used continuously while setting the driving temperature to a relatively high temperature of approximately 850° C., a problem in that a heater resistance value increases over time to eventually disable the sensor element is more likely to occur compared with a case where the driving temperature is low.

It is assumed, from intensive studies made by the inventors of the present invention, that the increase in heater resistance value is caused because Pt, which forms the heater element heated to a high temperature at the time of driving, changes into a gas phase, and diffuses in the porous insulating layer.

The configuration to prevent or reduce such diffusion of Pt during use is required to increase a sensor element lifetime, while the occurrence of cracking caused by the difference in coefficient of thermal expansion between the solid electrolyte layers and the insulating layer is required to be prevented or reduced, as required in the conventional sensor element.

Japanese Patent No. 3668050, Japanese Patent No. 3873302, Japanese Patent No. 4980996, Japanese Patent No. 3096281, and Japanese Patent No. 4573939 each neither disclose nor suggest prevention or reduction of diffusion of Pt when the sensor element is used.

SUMMARY

The present invention is directed to a sensor element formed of an oxygen-ion conductive solid electrolyte, and relates, in particular, to the configuration of a heater included in the sensor element.

According to the present invention, a planar sensor element included in a gas sensor for detecting a predetermined gas component in a measurement gas includes: a base part that is formed of an oxygen-ion conductive solid electrolyte; and a heater part that heats the sensor element. The heater part includes: a heater element that generates heat by being externally powered, and contains Pt; an insulating layer that includes 90 wt % to 99.9 wt % of an insulating material having a different coefficient of thermal expansion from the solid electrolyte; and a heater electrode that is located on a main surface of the sensor element to be exposed, and is electrically connected to the heater element. A portion of the heater part other than the heater electrode is buried in the base part. The heater element is covered with the insulating layer. The insulating layer has a porosity of 4% or less. The insulating layer has a thickness of 50 μm to 150 μm. The heater element has a thickness of 10 μm to 50 μm. A distance between an end portion of the sensor element and the insulating layer in a longitudinal direction of the sensor element is 0.25 mm to 0.75 mm. A distance between the main surface on which the heater electrode is located and the insulating layer in a direction of a thickness of the sensor element is 0.20 mm to 0.60 mm. A distance between a side surface of the sensor element and the insulating layer in a direction of a width of the sensor element is 0.20 mm to 0.60 mm. A total length of the sensor element in the longitudinal direction is 80.0 mm or less.

According to the present invention, when the sensor element is used continuously, and a temperature cycle including heating during use and cooling after use is repeated, diffusion of Pt and the occurrence of cracking caused by a difference in coefficient of thermal expansion between solid electrolyte layers and a heater insulating layer are suitably prevented or reduced, enabling the planar sensor element to have an increased lifetime.

An object of the present invention is thus to provide a sensor element having an increased lifetime due to prevention or reduction of diffusion of Pt during use and prevention or reduction of the occurrence of cracking caused by a difference in coefficient of thermal expansion between solid electrolyte layers and an insulating layer.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 shows procedures for forming a heater element 72 and a heater insulating layer 74 in more details.

DESCRIPTION OF THE PREFERRED EMBODIMENTS

<Schematic Configuration of Gas Sensor>

A schematic configuration of a gas sensor 100 including a sensor element 101 according to the present embodiment will be described first. Description is made in the present embodiment by taking, as an example, a case where the gas sensor 100 is a limiting current type NOx sensor that detects NOx and measures the concentration of NOx using the sensor element 101.

Figure 1:
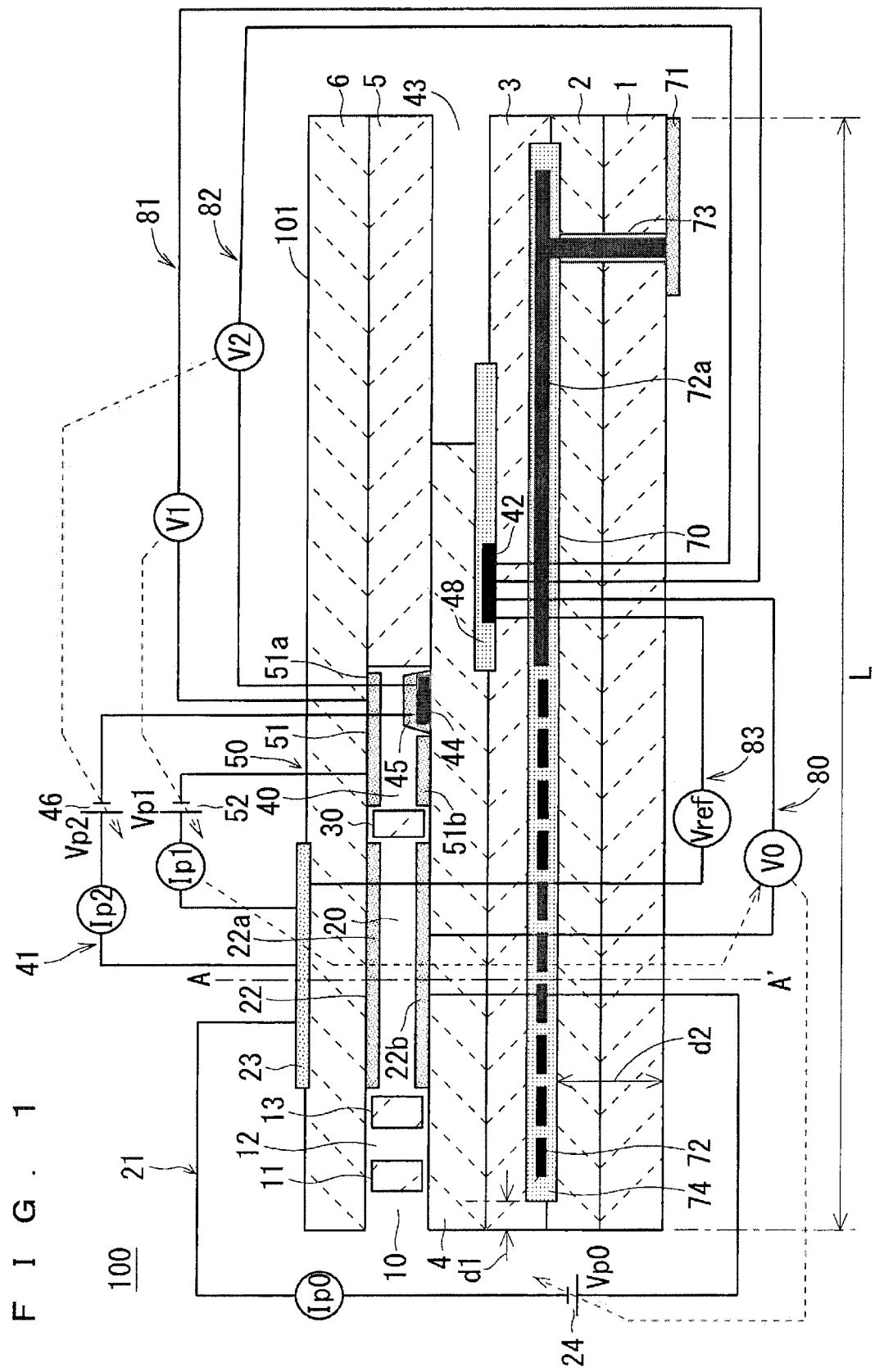
FIG. 1 schematically shows an example of the configuration of a gas sensor 100 including a vertical sectional view taken along the longitudinal direction of a sensor element 101.
Figure 2:
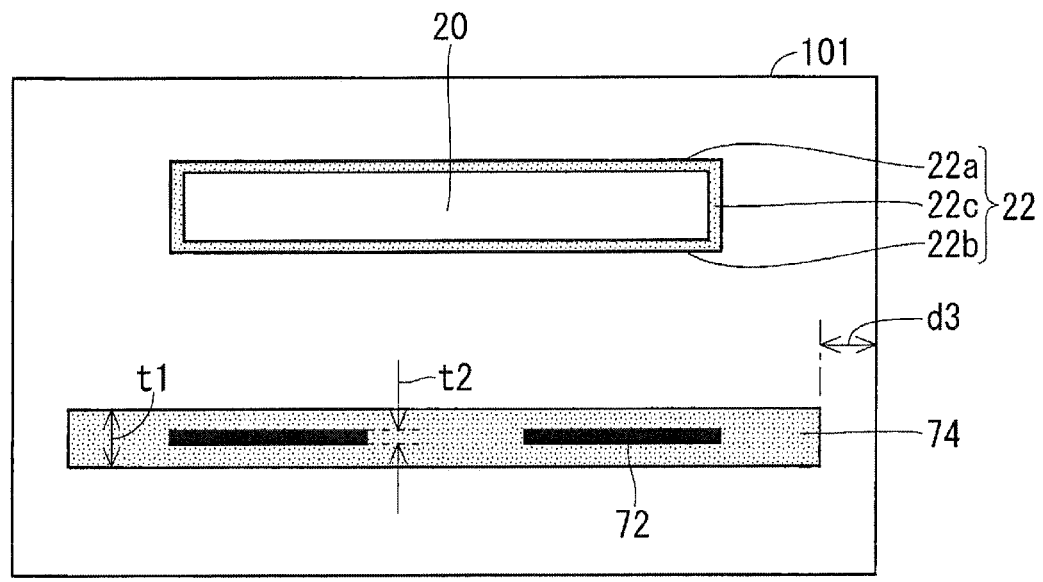
FIG. 2 is a schematic view of a cross section perpendicular to the longitudinal direction of the sensor element 101 taken along the line A-A' of FIG. 1.

FIG. 1 schematically shows an example of the configuration of the gas sensor 100 including a vertical sectional view taken along the longitudinal direction of the sensor element 101. FIG. 2 is a schematic view of a cross section perpendicular to the longitudinal direction of the sensor element 101 taken along the line A-A' of FIG. 1.

The sensor element 101 is a planar (an elongated plate-shaped) element having a structure in which six solid electrolyte layers, namely, a first substrate layer 1, a second substrate layer 2, a third substrate layer 3, a first solid electrolyte layer 4, a spacer layer 5, and a second solid electrolyte layer 6, each formed of zirconia ($ZrO_2$) (e.g., yttrium stabilized zirconia (YSZ)) being an oxygen-ion conductive solid electrolyte, are laminated in the stated order from the bottom side of FIG. 1. A solid electrolyte forming these six layers is dense and airtight. An upper surface and a lower surface of each of these six layers in FIG. 1 are hereinafter also simply referred to as an upper surface and a lower surface, respectively. A part of the sensor element 101 formed of a solid electrolyte as a whole is generically referred to as a base part.

The sensor element 101 is manufactured, for example, by performing predetermined machining and printing of circuit patterns with respect to ceramic green sheets corresponding to respective layers, then laminating these green sheets, and further firing the laminated green sheets for integration.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 that look as if they were provided by hollowing out the spacer layer 5, and that have an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (whose openings have longitudinal directions perpendicular to the page of FIG. 1). A part extending from the gas inlet 10 to the second internal space 40 is also referred to as a gas distribution part.

At a location farther from the end portion than the gas distribution part is, a reference gas introduction space 43 having a side portion defined by a side surface of the first solid electrolyte layer 4 is provided between an upper surface of the third substrate layer 3 and a lower surface of the spacer layer 5. For example, atmospheric air is introduced into the reference gas introduction space 43 as a reference gas when a NOx concentration is measured.

An atmospheric air introduction layer 48 is a layer formed of porous alumina, and the reference gas is introduced into the atmospheric air introduction layer 48 through the reference gas introduction space 43. The atmospheric air introduction layer 48 is formed to cover a reference electrode 42.

The reference electrode 42 is an electrode formed to be sandwiched between the upper surface of the third substrate layer 3 and the first solid electrolyte layer 4, and the atmospheric air introduction layer 48 leading to the reference gas introduction space 43 is provided around the reference electrode 42, as described above. As will be described below, an oxygen concentration (oxygen partial pressure) in the first internal space 20 and the second internal space 40 can be measured using the reference electrode 42.

In the gas distribution part, the gas inlet 10 opens to an external space, and a measurement gas is taken from the external space into the sensor element 101 through the gas inlet 10.

The first diffusion control part 11 is a part providing a predetermined diffusion resistance to the measurement gas taken through the gas inlet 10.

The buffer space 12 is a space provided to guide the measurement gas introduced from the first diffusion control part 11 to the second diffusion control part 13.

The second diffusion control part 13 is a part providing a predetermined diffusion resistance to the measurement gas introduced from the buffer space 12 into the first internal space 20.

When the measurement gas is introduced from the outside of the sensor element 101 into the first internal space 20, the measurement gas, which is abruptly taken into the sensor element 101 through the gas inlet 10 due to pressure fluctuation of the measurement gas in the external space (pulsation of exhaust pressure in a case where the measurement gas is an exhaust gas of a vehicle), is not directly introduced into the first internal space 20, but is introduced into the first internal space 20 after the concentration fluctuation of the measurement gas is canceled through the first diffusion control part 11, the buffer space 12, and the second diffusion control part 13. This makes the concentration fluctuation of the measurement gas introduced into the first internal space 20 almost negligible.

The first internal space 20 is provided as a space used to adjust oxygen partial pressure in the measurement gas introduced through the second diffusion control part 13. The oxygen partial pressure is adjusted by operation of a main pump cell 21.

The main pump cell 21 is an electrochemical pump cell constituted by an inner pump electrode 22, an outer pump electrode 23, and the second solid electrolyte layer 6 sandwiched between the inner pump electrode 22 and the outer pump electrode 23. The inner pump electrode 22 has a ceiling electrode portion 22a that is provided substantially on the entire lower surface of a portion of the second solid electrolyte layer 6 facing the first internal space 20. The outer pump electrode 23 is provided in a region, on an upper surface of the second solid electrolyte layer 6 (one main surface of the sensor element 101), corresponding to the ceiling electrode portion 22a so as to be exposed to the external space.

The inner pump electrode 22 is formed over upper and lower solid electrolyte layers (the second solid electrolyte layer 6 and the first solid electrolyte layer 4) that define the first internal space 20, and the spacer layer 5 that provides a side wall to the first internal space 20. Specifically, the ceiling electrode portion 22a is formed on the lower surface of the second solid electrolyte layer 6, which provides a ceiling surface to the first internal space 20, a bottom electrode portion 22b is formed on the upper surface of the first solid electrolyte layer 4, which provides a bottom surface to the first internal space 20, and a side electrode portion 22c (FIG. 2) is formed on a side wall surface (internal surface) of the spacer layer 5 that forms opposite side wall portions of the first internal space 20, so as to connect the ceiling electrode portion 22a and the bottom electrode portion 22b. The inner pump electrode 22 is thus provided in the form of a tunnel at a location where the side electrode portion is provided.

The inner pump electrode 22 and the outer pump electrode 23 are each formed as a porous cermet electrode (e.g., a cermet electrode formed of $ZrO_2$ and Pt that contains Au of 1%). The inner pump electrode 22 to be in contact with the measurement gas is formed using a material having a weakened reducing ability with respect to a NOx component in the measurement gas.

The main pump cell 21 can pump out oxygen in the first internal space 20 to the external space or pump in oxygen in the external space to the first internal space 20 by applying, using a variable power supply 24, a desired pump voltage Vp0 across the inner pump electrode 22 and the outer pump electrode 23 to allow a pump current Ip0 to flow between the inner pump electrode 22 and the outer pump electrode 23 in a positive or negative direction.

To detect an oxygen concentration (oxygen partial pressure) in the atmosphere existing in the first internal space 20, the inner pump electrode 22, the second solid electrolyte layer 6, the spacer layer 5, the first solid electrolyte layer 4, the third substrate layer 3, and the reference electrode 42 constitute an electrochemical sensor cell, namely, a main-pump-control oxygen-partial-pressure detection sensor cell 80.

The oxygen concentration (oxygen partial pressure) in the first internal space 20 can be obtained by measuring electromotive force V0 in the main-pump-control oxygen-partial-pressure detection sensor cell 80.

Furthermore, the pump current Ip0 is controlled by performing feedback control of the voltage Vp0 so that the electromotive force V0 is maintained constant. The oxygen concentration in the first internal space 20 is thereby maintained to have a predetermined constant value.

The third diffusion control part 30 is a part providing a predetermined diffusion resistance to the measurement gas having an oxygen concentration (oxygen partial pressure) controlled by the operation of the main pump cell 21 in the first internal space 20, and guiding the measurement gas to the second internal space 40.

The second internal space 40 is provided as a space to perform processing concerning measurement of a nitrogen oxide (NOx) concentration in the measurement gas introduced through the third diffusion control part 30. The NOx concentration is measured, mainly in the second internal space 40 in which an oxygen concentration has been adjusted by an auxiliary pump cell 50, by the operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part in the second internal space 40. Owing to such adjustment, the oxygen concentration in the second internal space 40 can be maintained constant with high precision, and thus the gas sensor 100 is enabled to measure the NOx concentration with high precision.

The auxiliary pump cell 50 is an auxiliary electrochemical pump cell constituted by an auxiliary pump electrode 51, the outer pump electrode 23 (not limited to the outer pump electrode 23 but may be any appropriate electrode outside the sensor element 101), and the second solid electrolyte layer 6. The auxiliary pump electrode 51 has a ceiling electrode portion 51a that is provided substantially on the entire lower surface of a portion of the second solid electrolyte layer 6 facing the second internal space 40.

The auxiliary pump electrode 51 is provided in the second internal space 40 in the form of a tunnel, as with the inner pump electrode 22 provided in the first internal space 20 described previously. That is to say, the ceiling electrode portion 51a is formed on the second solid electrolyte layer 6, which provides a ceiling surface to the second internal space 40, a bottom electrode portion 51b is formed on the first solid electrolyte layer 4, which provides a bottom surface to the second internal space 40, and a side electrode portion (not illustrated) that connects the ceiling electrode portion 51a and the bottom electrode portion 51b is formed on opposite wall surfaces of the spacer layer 5, which provides a side wall to the second internal space 40. The auxiliary pump electrode 51 is thus provided in the form of a tunnel.

As with the inner pump electrode 22, the auxiliary pump electrode 51 is formed using a material having a weakened reducing ability with respect to a NOx component in the measurement gas.

The auxiliary pump cell 50 can pump out oxygen in the atmosphere existing in the second internal space 40 to the external space or pump in oxygen existing in the external space to the second internal space 40 by applying a desired voltage Vp1 across the auxiliary pump electrode 51 and the outer pump electrode 23.

In order to control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an auxiliary-pump-control oxygen-partial-pressure detection sensor cell 81.

The auxiliary pump cell 50 performs pumping using a variable power supply 52 whose voltage is controlled based on electromotive force V1 detected by the auxiliary-pump-control oxygen-partial-pressure detection sensor cell 81. The oxygen partial pressure in the atmosphere in the second internal space 40 is thereby controlled to a low partial pressure having substantially no effect on measurement of NOx.

At the same time, a resulting pump current Ip1 is used to control electromotive force in the main-pump-control oxygen-partial-pressure detection sensor cell 80. Specifically, the pump current Ip1 is input, as a control signal, into the main-pump-control oxygen-partial-pressure detection sensor cell 80, and, through control of the electromotive force V0 thereof, the oxygen partial pressure in the measurement gas introduced through the third diffusion control part 30 into the second internal space 40 is controlled to have a gradient that is always constant. In use as a NOx sensor, the oxygen concentration in the second internal space 40 is maintained to have a constant value of approximately 0.001 ppm by the action of the main pump cell 21 and the auxiliary pump cell 50.

The measurement pump cell 41 measures the NOx concentration in the measurement gas in the second internal space 40. The measurement pump cell 41 is an electrochemical pump cell constituted by a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 also functions as a NOx reduction catalyst that reduces NOx existing in the atmosphere in the second internal space 40. Furthermore, the measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of nitrogen oxides in the atmosphere around the measurement electrode 44, and detect the amount of generated oxygen as a pump current Ip2.

In order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely, a measurement-pump-control oxygen-partial-pressure detection sensor cell 82. A variable power supply 46 is controlled based on electromotive force V2 detected by the measurement-pump-control oxygen-partial-pressure detection sensor cell 82.

The measurement gas introduced into the second internal space 40 reaches the measurement electrode 44 through the fourth diffusion control part 45 under a condition in which the oxygen partial pressure is controlled. Nitrogen oxides in the measurement gas around the measurement electrode 44 are reduced ($2NO \rightarrow N_2+O_2$) to generate oxygen. The generated oxygen is pumped by the measurement pump cell 41, and, at that time, a voltage Vp2 of the variable power supply 46 is controlled so that a control voltage V2 detected by the measurement-pump-control oxygen-partial-pressure detection sensor cell 82 is maintained constant. The amount of oxygen generated around the measurement electrode 44 is proportional to a nitrogen oxide concentration in the measurement gas, and thus the nitrogen oxide concentration in the measurement gas is calculated using the pump current Ip2 in the measurement pump cell 41.

If the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference atmospheric air can be detected, and the concentration of the NOx component in the measurement gas can thereby be obtained.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure in the measurement gas outside the sensor can be detected using electromotive force Vref obtained by the sensor cell 83.

In the gas sensor 100 having such a configuration, the measurement gas in which the oxygen partial pressure is always maintained to have a constant low value (value having substantially no effect on measurement of NOx) by operation of the main pump cell 21 and the auxiliary pump cell 50 is provided to the measurement pump cell 41. The NOx concentration in the measurement gas can be known based on the fact that the pump current Ip2 flowing by the measurement pump cell 41 pumping out oxygen generated through reduction of NOx performed by the measurement electrode 44 is approximately proportional to the concentration of NOx in the measurement gas.

<Heater Part>

Figure 3:
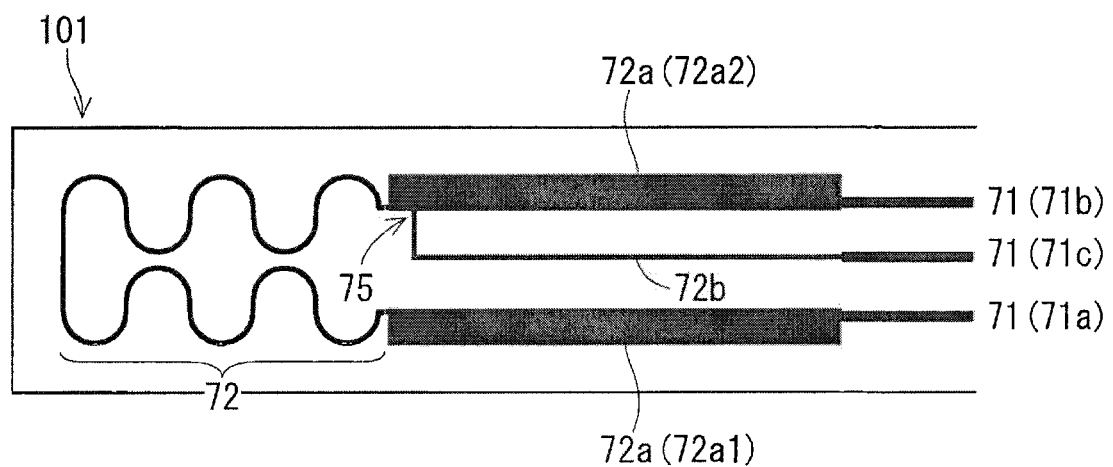
FIG. 3 shows a schematic planar arrangement of principal components of a heater part 70.

The sensor element 101 further includes a heater part 70 playing a role in temperature adjustment of heating the sensor element 101 and keeping it warm, in order to enhance the oxygen ion conductivity of the solid electrolyte forming the base part. FIG. 3 shows a schematic planar arrangement of principal components of the heater part 70.

The heater part 70 includes heater electrodes 71 (71a, 71b, and 71c), a heater element 72, heater leads 72a (72a1 and 72a2), a resistance detection lead 72b, through holes 73, and a heater insulating layer 74. In FIG. 3, however, the through holes 73 and the heater insulating layer 74 are omitted. A portion of the heater part 70 other than the heater electrodes 71 is buried in the base part of the sensor element 101.

The heater electrodes 71 (71a, 71b, and 71c) are electrodes formed to be in contact with a lower surface of the first substrate layer 1 (the other main surface of the sensor element 101).

The heater element 72 is a resistive heating element located between the second substrate layer 2 and the third substrate layer 3. The heater element 72 generates heat by being powered from the outside of the sensor element 101 through the heater electrodes 71, the through holes 73, and the heater leads 72a, which constitute a current-carrying path. The heater element 72 is formed of Pt, or formed to contain Pt as a main component. The heater element 72 is buried, in a predetermined range of the sensor element 101 in which the gas distribution part is provided, opposite to the gas distribution part in a direction of the thickness of the element.

A pair of heater leads (the heater leads 72a1 and 72a2) connected to the respective ends of the heater element 72 is provided to have approximately the same shape, that is, to have the same resistance value. The heater leads 72a1 and 72a2 are respectively connected to the heater electrodes 71a and 71b through corresponding through holes 73.

Furthermore, the resistance detection lead 72b is provided to be drawn from a connection portion 75 at which the heater element 72 and the heater lead 72a2 are connected. Assume that a resistance value of the resistance detection lead 72b is negligible. The resistance detection lead 72b is connected to the heater electrode 71c through a corresponding through hole 73.

In the sensor element 101, each component of the sensor element 101 can be heated to a predetermined temperature and kept warm by allowing a current to flow between the heater electrodes 71a and 71b to perform heating using the heater element 72. Specifically, the sensor element 101 is heated so that the solid electrolyte around the gas distribution part is at a temperature of approximately 750° C. to 950° C. The oxygen ion conductivity of the solid electrolyte forming the base part in the sensor element 101 is enhanced by the heating.

Since the heater leads 72a1 and 72a2 have the same resistance value, and the resistance value of the resistance detection lead 72b is negligible, when $R_1$ denotes the resistance value between the heater electrodes 71a and 71b, and $R_2$ denotes the resistance value between the heater electrodes 71b and 71c, the resistance value (heater resistance value) $R_H$ of the heater element 72 is calculated by the following equation:

$$R_H = R_1 - R_2 \quad (1)$$

The heater resistance value is used to control the heating temperature when heating is performed using the heater element 72.

The heater insulating layer 74 is an insulating layer formed to cover the heater element 72. The heater insulating layer 74 is formed for electrical insulation between the second substrate layer 2 and the heater element 72 and for electrical insulation between the third substrate layer 3 and the heater element 72.

The heater insulating layer 74 contains 90 wt % to 99.9 wt % of $Al_2O_3$ (α-alumina) as a main component. The heater insulating layer 74 also contains, as sub components, a compound of Si and a compound of Mg respectively derived from $SiO_2$ and $MgCO_3$ contained in a raw powder as sintering aids. The compound of Si and the compound of Mg are preferably contained in equal amounts. In addition, in the present embodiment, the heater insulating layer 74 is provided as a densified layer having a porosity of 4.0% or less, preferably 2.0% or less.

The porosity of the heater insulating layer 74 of 4.0% or less is achieved by using a specific material as a material for $Al_2O_3$ as the main component, and by setting firing conditions when the sensor element 101 is eventually obtained to specific conditions. Details will be described below.

In the present embodiment, assume that the porosity of the heater insulating layer 74 is calculated by capturing, using an SEM, an image of a cross section of the sensor element 101, including the heater element 72, perpendicular to the longitudinal direction of the sensor element 101 after polishing, and binarizing an SEM image as obtained.

The reason that the heater insulating layer 74 is provided as the densified layer is to prevent diffusion of Pt, which forms the heater element 72, into pores of the heater insulating layer 74 when the sensor element 101 is used. In the sensor element 101 according to the present embodiment, the heater insulating layer 74 is provided as the densified layer having a porosity of 4.0% or less, so that damage to the heater element 72 caused by diffusion of Pt is suitably prevented or reduced even if the sensor element 101 is used continuously. The sensor element thus has an increased lifetime, compared with the conventional sensor element.

Whether Pt diffuses from the heater element 72 or not can directly be determined by actually exposing the heater insulating layer 74 of the sensor element 101 after use for a given period of time, and observing an image and analyzing the composition of the exposed heater insulating layer using the SEM and the like, and also can be known from an increase rate of a heater resistance value R (resistance increase rate) after use when a heater resistance value R0 before use (in an initial stage of use) is used as a reference, which is calculated by the following equation (2):

$$\text{resistance increase rate } (\%) = 100 \times (R - R0)/R0 \quad (2)$$

The heater resistance value is an electrical resistance value on a path of a heater current from one of the heater electrodes 71 to the other one of the heater electrodes 71, and it is confirmed in advance that the heater resistance value can vary mainly due to diffusion of Pt from the heater element 72. Thus, by measuring the heater resistance value both in the initial stage of use and after use, and determining whether the resistance increase rate calculated by the equation (2) exceeds a predetermined threshold or not, whether Pt diffuses from the heater element 72 or not can be determined using the sensor element 101 without breaking the sensor element 101.

Specifically, it is determined that Pt diffuses from the heater element 72 when the resistance increase rate is 2% or more. In the sensor element 101 according to the present embodiment, in which the heater insulating layer 74 has a porosity of 4.0% or less, the resistance increase rate calculated by the equation (2) is limited to less than 2%. When the heater insulating layer 74 has a porosity of 2.0% or less, the resistance increase rate is limited to 0.7% or less.

As mentioned in Japanese Patent No. 4573939, it has been considered that, in the case that the insulating layer containing alumina as the main component is provided as the densified layer in a planar sensor element similar to the sensor element 101 according to the present embodiment, cracking caused by a difference in coefficient of thermal expansion between the heater insulating layer and the solid electrolyte layers occurs as a result of repeating a temperature cycle including heating during use and cooling after use. Zirconia has a coefficient of thermal expansion of approximately 10 to 11 ($\times 10^{-6}/°$ C.), whereas alumina's coefficient of thermal expansion is approximately 7 to 9 ($\times 10^{-6}/°$C).

However, in the sensor element 101 according to the present embodiment, although it is planar and includes the densified heater insulating layer 74, the occurrence of cracking caused by the difference in coefficient of thermal expansion between the heater insulating layer 74 and the solid electrolyte layers (in particular, the second substrate layer 2 and the third substrate layer 3) is suitably prevented or reduced by setting the dimensions of each component shown below to values in the following ranges:

the thickness t1 of the heater insulating layer 74: 50 μm to 150 μm;

the thickness t2 of the heater element 72: 10 μm to 50 μm;

a distance (hereinafter, an end portion distance) d1 between an end portion of the sensor element 101 and the heater insulating layer 74 in the longitudinal direction of the sensor element 101 (the horizontal direction in FIG. 1): 0.25 mm to 0.75 mm;

a distance (≈the sum of the thickness of the first substrate layer 1 and the thickness of the second substrate layer 2, hereinafter, a thickness direction distance) d2 between the other main surface (a main surface on which the heater electrodes 71 are located) and the heater insulating layer 74 in a direction of the thickness of the sensor element 101 (the vertical direction in FIG. 1): 0.20 mm to 0.60 mm;

a distance (hereinafter, a side portion distance) d3 between a side surface of the sensor element 101 and the heater insulating layer 74 in a direction of the width of the sensor element 101 (the horizontal direction in FIG. 2): 0.20 mm to 0.60 mm; and the total length L of the sensor element 101 in the longitudinal direction: 80.0 mm or less.

These conditions relating to the dimensions of each component of the sensor element 101 are hereinafter generically referred to as sensor element dimensional conditions. It can be said that the sensor element 101 according to the present embodiment has an increased lifetime also from the viewpoint of prevention or reduction of the occurrence of cracking due to satisfaction of the sensor element dimensional conditions.

A range of the thickness t2 of the heater element 72 in the sensor element dimensional conditions is determined so that the heater resistance value becomes a value within a predetermined range determined from the viewpoint of performance, a lifetime, and the like of the sensor element 101.

The thickness t1 of the heater insulating layer 74 has a value including the thickness of the heater element 72 existing inside the heater insulating layer 74. Setting a value of the thickness t1 of the heater insulating layer 74 to a value greater than the upper limit in the sensor element dimensional conditions is not preferable because stress caused by the difference in coefficient of thermal expansion between the heater insulating layer 74 and the solid electrolyte layers (in particular, the second substrate layer 2 and the third substrate layer 3) increases, and, as a result, cracking is likely to occur in the sensor element 101. On the other hand, setting the value of the thickness t1 of the heater insulating layer 74 to a value smaller than the lower limit in the sensor element dimensional conditions is not preferable because insulation is not sufficiently ensured, and a leakage of the heater current flowing through the heater element 72 may be caused. The thickness t1, however, may not necessarily be constant, and may differ at a location at which the heater element 72 exists and at a location at which the heater element 72 does not exist.

Furthermore, setting values of the end portion distance d1, the thickness direction distance d2, and the side portion distance d3, which define the location of the heater insulating layer 74 in the base part, to values smaller than the respective lower limits in the sensor element dimensional conditions is not preferable because the sensor element 101 decreases in strength, and cracking caused by the stress caused by the difference in coefficient of thermal expansion between the heater insulating layer 74 and the solid electrolyte layers (in particular, the second substrate layer 2 and the third substrate layer 3) is likely to occur. The lower limit of the total length L of the sensor element 101 is determined appropriately from design requirements for the sensor element 101.

On the other hand, setting the values of the end portion distance d1, the thickness direction distance d2, the side portion distance d3, and the total length L of the sensor element 101 to values greater than the respective upper limits in the sensor element dimensional conditions is not preferable because it is necessary to allow a larger heater current to flow for heating due to an increase in dimensions of the element, leading to an increase in leakage current.

<Process of Manufacturing Sensor Element>

The process of manufacturing the sensor element 101 having a configuration and features as described above will be described next. In the present embodiment, the sensor element 101 is manufactured by forming a laminated body formed of green sheets containing an oxygen-ion conductive solid electrolyte, such as zirconia, as a ceramic component, and by cutting and firing the laminated body.

A case where the sensor element 101 including the six layers illustrated in FIG. 1 is manufactured will be described, as an example, below. In this case, six green sheets corresponding to the first substrate layer 1, the second substrate layer 2, the third substrate layer 3, the first solid electrolyte layer 4, the spacer layer 5, and the second solid electrolyte layer 6 are prepared.

Figure 4:
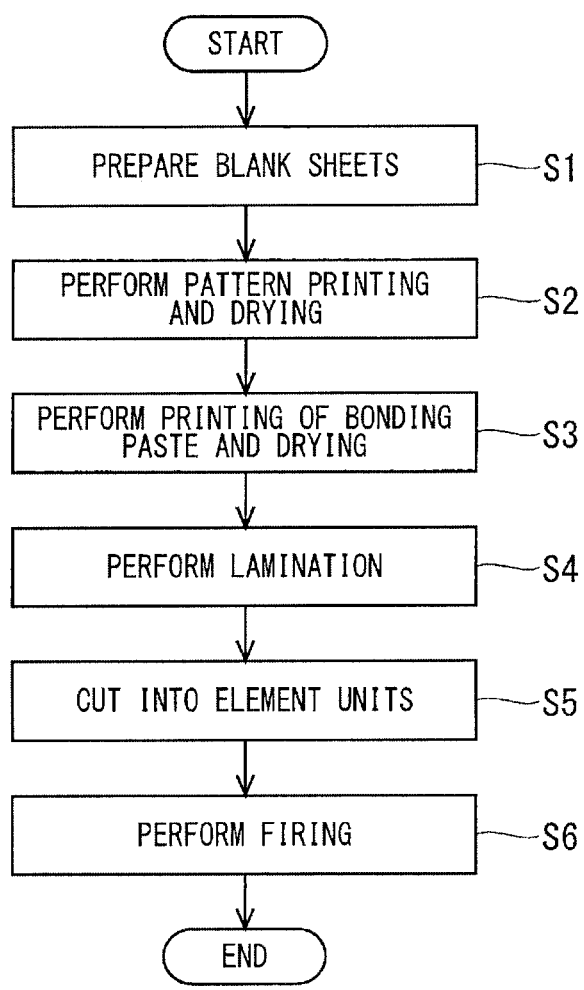
FIG. 4 is a flowchart showing processing performed when the sensor element 101 is manufactured.

FIG. 4 is a flowchart showing processing performed when the sensor element 101 is manufactured. FIG. 5 shows procedures for forming the heater element 72 and the heater insulating layer 74 in more details.

In the manufacture of the sensor element 101, blank sheets (not illustrated) that are green sheets having no pattern formed thereon are prepared first (step S1). In the manufacture of the sensor element 101 including the six layers, six blank sheets corresponding to the respective layers are prepared. The blank sheets have a plurality of sheet holes used for positioning in printing and lamination. The sheet holes are formed in advance through, for example, punching by a punching machine when the sheets for the respective layers are in the form of the blank sheets prior to pattern formation. Green sheets corresponding to layers forming an internal space also include penetrating portions corresponding to the internal space formed in advance through, for example, punching as described above. The blank sheets corresponding to the respective layers of the sensor element 101 are not required to have the same thickness.

After preparation of the blank sheets corresponding to the respective layers, pattern printing and drying are performed on the individual blank sheets (step S2). A known screen printing technique can be used for printing of patterns and adhesives. A known drying means can be used for drying after printing.

As for formation of a pattern (hereinafter, a heater pattern) that becomes the heater element 72, the heater leads 72a, and the resistance detection lead 72b and a pattern that becomes the heater insulating layer 74, for example, a blank sheet that becomes the second substrate layer 2 after firing is prepared first as a target of printing, as shown in FIG. 5 (step S21). Considering deformation of the blank sheet and the like caused by repetition of printing, a laminate (preceding laminated sheet) of the blank sheet that becomes the first substrate layer 1 and the blank sheet that becomes the second substrate layer 2 may be prepared in advance.

When the blank sheet or the preceding laminated sheet is prepared, a paste for heater insulating layer formation (hereinafter, an insulating paste) is printed in a predetermined pattern to form, on the blank sheet or the preceding laminated sheet, a portion of the heater insulating layer 74 adjacent to the second substrate layer 2 (step S22). The printing may be repeated a plurality of times depending on the thickness of the heater insulating layer 74 to be formed.

Used as the insulating paste is a paste obtained by mixing an inorganic mixed powder, which is obtained in advance by wet mixing $Al_2O_3$ (α-alumina) as the main component with $SiO_2$ and $MgCO_3$ added as the sintering aids and then drying the mixture, with a binder component (a dispersant, an organic solvent, a polyvinyl butyral resin, and a nonionic surfactant) dissolved in advance, and adjusting the mixture to have a predetermined viscosity.

At the time, as a raw powder for $Al_2O_3$ (α-alumina), α-alumina having an average particle size of 0.05 m to 0.4 μm and a specific surface area of approximately 10 $m^2/g$ to 30 $m^2/g$ is used. By the use of the raw powder satisfying the requirements and the presence of the sintering aids, the heater insulating layer 74 that is dense to have a porosity of 4.0% or less and can prevent or reduce diffusion of Pt can be provided. If the raw powder for $Al_2O_3$ is different, for example, if α-alumina not satisfying the above-mentioned requirements, transition alumina including γ-alumina or θ-alumina as a main phase, or the like is used as the raw powder, it is difficult to form the heater insulating layer 74 that is dense to be able to prevent or reduce diffusion of Pt.

When the insulating paste is printed in the pattern, a paste for heater pattern formation is printed so as to be laminated to form the heater pattern on the pattern of the insulating paste (step S23). In forming the heater pattern, different pastes may be used depending on a target of formation (the heater element 72, the heater leads 72a, and the resistance detection lead 72b).

Finally, the insulating paste is printed again in a predetermined pattern to form a portion of the heater insulating layer 74 adjacent to the third substrate layer 3 (step S24). At the time, the insulating paste is printed so that the heater pattern is concealed between a pattern to be formed and the pattern of the insulating paste printed previously. At a location at which the heater pattern does not exist, the pattern in which the insulating paste is printed later is superimposed on the pattern in which the insulating paste is printed previously. The printing may also be repeated a plurality of times depending on the thickness of the heater insulating layer 74 to be formed.

More specifically, the patterns are formed using the insulating paste and the paste for heater pattern formation in view of contraction at the time of firing so that they satisfy in the resulting sensor element 101 conditions other than the condition relating to the total length L of the sensor element 101 in the above-mentioned sensor element dimensional conditions. Patterns of other components, such as various electrodes, are also formed on conditions that targets of formation are formed to have predetermined sizes in the resulting sensor element 101.

After pattern printing on each of the blank sheets, printing of a bonding paste and drying are performed to laminate and bond the green sheets corresponding to the respective layers (step S3).

Then, the green sheets to which an adhesive has been applied are stacked in a predetermined order, and the stacked green sheets are crimped under predetermined temperature and pressure conditions to thereby form a laminated body (step S4). Crimping yields a state in which the heater pattern and the pattern for heater insulating layer formation covering the heater pattern are sandwiched between the green sheet that becomes the second substrate layer 2 after firing and the green sheet that becomes the third substrate layer 3 after firing.

Specifically, crimping is performed by stacking and holding the green sheets as a target of lamination in a predetermined lamination jig (not illustrated) while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be set appropriately to achieve good lamination.

After the laminated body is obtained as described above, the laminated body is cut out at a plurality of locations to obtain individual units (referred to as element bodies) of the sensor element 101 (step S5). More specifically, the laminated body is cut out in view of contraction at the time of firing so that the resulting sensor element 101 satisfies the sensor element dimensional conditions relating to the total length L.

The cut out element bodies are fired at a firing temperature of approximately 1300° C. to 1500° C. (step S6). As a result, the sensor element 101 that includes the heater insulating layer 74 formed as the densified layer having a porosity of 4.0% or less and satisfies the above-mentioned sensor element dimensional conditions is generated.

The sensor element 101 thus obtained is housed in a predetermined housing, and incorporated into a main body (not illustrated) of the gas sensor 100.

As described above, according to the present embodiment, the planar sensor element including the heater part inside the base part formed of a solid electrolyte satisfies the above-mentioned sensor element dimensional conditions while including the heater insulating layer formed as the densified layer having a porosity of 4.0% or less. This suitably prevents or reduces diffusion of Pt and the occurrence of cracking caused by the difference in coefficient of thermal expansion between the solid electrolyte layers and the heater insulating layer when the sensor element is used continuously and the temperature cycle including heating during use and cooling after use is repeated. This means that, according to the present embodiment, the planar sensor element has an increased lifetime.

<Modifications>

In the above-mentioned embodiment, description is made by taking, as an example, a case where the sensor element 101 is a planar sensor element having a series two-chamber structure included in the limiting current NOx sensor. However, an embodiment of forming of a sensor element so that the sensor element satisfies the sensor element dimensional conditions while including the heater insulating layer formed as the densified layer in order to increase a lifetime of the sensor element is applicable not only to a sensor element having a similar structure and detecting another gas species but also to various planar sensor elements in which the sensor part and the heater part are integrally formed.

For example, the embodiment may be applied to a sensor element having three internal spaces and included in a limiting current gas sensor, a sensor element having internal spaces arranged in a different manner from that in the above-mentioned embodiment, or a sensor element included in a mixed potential gas sensor.

EXAMPLES

A total of 21 types (all Examples and all Comparative Examples) of sensor elements 101 having different combinations of conditions to manufacture the insulating paste for forming the heater insulating layer 74, the porosity of the heater insulating layer 74, and the dimensions at the six locations of the sensor element 101 directed to the sensor element dimensional conditions (the thickness t1 of the heater insulating layer 74, the thickness t2 of the heater element 72, the end portion distance d1, the thickness direction distance d2, the side portion distance d3, and the total length L of the sensor element 101) were manufactured. For each of the sensor elements 101, a durability test was conducted through continuous heating using the heater part 70 for a long period of time, and the state after the test was evaluated.

As for the conditions to manufacture the insulating paste, a material species of $Al_2O_3$ (alumina) used as a material was set to be at two levels, and an additive rate (a composition ratio) of the (sintering) aids was set to be at four levels of 0.1 wt %, 6 wt %, 10 wt %, and 15 wt %. As for the material species of alumina, a material species satisfying the above-mentioned requirements of α-alumina having an average particle size of 0.05 μm to 0.4 μm and a specific surface area of approximately 10 $m^2/g$ to 30 $m^2/g$ is hereinafter referred to as a material species "A", and a material species having an average particle size of 0.5 μm to 1.0 μm and a specific surface area of approximately 70 $m^2/g$ to 100 $m^2/g$ is hereinafter referred to as a material species "B". The material species "B" can be used to form a porous heater insulating layer included in the conventional sensor element.

The insulating paste was manufactured in the following manner. First, a powder of $Al_2O_3$ as the main component, powders of $SiO_2$ and $MgCO_3$ as the sintering aids, IPA as a solvent, and cobbles made of $Al_2O_3$ were put into a pot mixer having a volume of 1 L, and a mixture obtained by mixing them in the pot mixer at 100 rpm for 24 hours was dried to obtain an inorganic mixed powder. The inorganic mixed powder and the binder component (dispersant, organic solvent, polyvinyl butyral resin, and nonionic surfactant) dissolved by being agitated by an automatic orbital agitator for four minutes were agitated and mixed by the automatic orbital agitator for 15 minutes using the cobbles made of $Al_2O_3$, thereby to obtain an insulating paste having a disintegration degree of 50 μm or less and a viscosity of 20 Pa-s to 40 Pa-s. In each of Examples and Comparative Examples, $SiO_2$ and $MgCO_3$ were in equal amounts.

The porosity of the heater insulating layer 74 was set to be at two levels of 2.0% and 4.0% for the sensor elements 101 in which the material species of alumina was set to "A". Conditions to manufacture the sensor element 101 (conditions to fire the element body) when the porosity was 4.0% were experimentally specified in advance, and the sensor element 101 in which the porosity was 2.0% was manufactured by changing the manufacturing conditions using the specified conditions as reference conditions. Specifically, the porosities at the two levels of 2.0% and 4.0% were achieved by performing a predetermined firing profile in which the firing temperature was changed within a range of approximately 1300° C. to 1500° C.

On the other hand, as for the sensor elements 101 in which the material species of alumina was set to "B", two levels of the sensor elements 101 were manufactured, including the sensor element 101 manufactured under the same conditions as the reference conditions for the material species "A" and the sensor element 101 manufactured by adjusting the firing conditions so that the porosity was smaller compared with a case where the firing conditions were the same as the reference conditions.

The porosity of the heater insulating layer 74 was specified in the following manner. First, an SEM image (a reflected electronic image at a magnification of 1000 times and a resolution of 1.2 million pixels) of a cross section perpendicular to the longitudinal direction of the sensor element 101 and including the heater element 72 was captured after polishing the cross section so that no particle fell. Two areas of the heater insulating layer 74 in the SEM image of the cross section each having an area of 2000 $μm^2$ or more were specified as porosity calculation areas, and values of the porosity were calculated for the respective two areas through image processing. An average value of the obtained two values was set to the porosity in Example or Comparative Example.

The porosity was calculated through image processing using Image-Pro Premier 9.2 (from Nippon Roper K. K.) as software. Specifically, for each of the porosity calculation areas, binarization and mask image generation were performed so that a portion other than pores became a mask area, an area ratio (%) of an area other than the mask area was obtained, and a value of the area ratio was set to the porosity for the porosity calculation area.

The dimensions at the total of six locations directed to the sensor element dimensional conditions (the thickness t1 of the heater insulating layer 74, the thickness t2 of the heater element 72, the end portion distance d1, the thickness direction distance d2, the side portion distance d3, and the total length L of the sensor element 101) were set to be at the following different levels:

t1: at five levels of 40 μm, 50 μm, 100 μm, 150 μm, and 160 μm;

t2: at five levels of 5 μm, 10 μm, 30 μm, 50 μm, and 60 μm;

d1: at five levels of 0.20 mm, 0.25 mm, 0.50 mm, 0.75 mm, and 0.80 mm;

d2: at five levels of 0.16 mm, 0.20 mm, 0.40 mm, 0.60 mm, and 0.70 mm;

d3: at five levels of 0.16 mm, 0.20 mm, 0.40 mm, 0.60 mm, and 0.70 mm; and

L: at three levels of 60.0 mm, 80.0 mm, and 90.0 mm.

From among the total of 21 types of sensor elements 101 having different combinations of the manufacturing conditions based on the above-mentioned description, the sensor elements 101 in which the material species of $Al_2O_3$ (alumina) is the material species "A", the additive rate of the aids satisfies a range of 0.1 wt % to 10 wt %, the porosity of the heater insulating layer 74 is 4.0% or less, and all the above-mentioned sensor element dimensional conditions relating to t1, t2, d1, d2, d3, and L are satisfied correspond to Examples (Examples 1 to 11), and the sensor elements 101 that do not meet at least one of these requirements correspond to Comparative Examples (Comparative Examples 1 to 10).

The durability test was conducted on condition that heating was performed continuously using the heater element 72 at 900° C. for 2000 hours. With respect to the sensor element 101 after the durability test, whether cracking occurred or not was determined, a value of the leakage current was measured, and whether Pt diffused in the heater insulating layer 74 or not was determined based on the SEM image, and besides, the heater resistance values before and after the test were measured, and the resistance increase rate after the test was calculated by substituting the results of measurement into the equation (2).

The leakage current was measured by applying a constant voltage across the heater electrode 71 and the outer pump electrode 23 in a state in which the sensor element 101 was heated to approximately 700° C. to 900° C. using the heater element 72, and measuring a current generated between the electrodes.

Conditions to form the sensor elements 101 according to Examples 1 to 11 and various evaluation results are listed in Table 1. Conditions to form the sensor elements 101 according to Comparative Examples 1 to 10 and various evaluation results are listed in Table 2. In Tables 1 and 2, the heater insulating layer 74 is simply indicated as an "INSULATING LAYER", and the heater element 72 is simply indicated as a "HEATER".

TABLE 1

|  |  | EXAMPLE 1 | EXAMPLE 2 | EXAMPLE 3 | EXAMPLE 4 | EXAMPLE 5 | EXAMPLE 6 |
|---|---|---|---|---|---|---|---|
| INSULATING LAYER | ALUMINA MATERIAL SPECIES | A | A | A | A | A | A |
|  | ADDITIVE RATE OF AIDS (wt %) | 6.0 | 6.0 | 6.0 | 6.0 | 6.0 | 6.0 |
|  | POROSITY (%) | 4.0 | 2.0 | 4.0 | 4.0 | 4.0 | 4.0 |
|  | THICKNESS t1 (μm) | 100 | 100 | 50 | 150 | 100 | 100 |
| HEATER LAYER | THICKNESS t2 (μm) | 30 | 30 | 30 | 30 | 10 | 50 |
| SIZE OF EACH COMPONENT OF SENSOR ELEMENT | d1 (mm) | 0.50 | 0.50 | 0.50 | 0.50 | 0.50 | 0.50 |
|  | d2 (mm) | 0.40 | 0.40 | 0.40 | 0.40 | 0.40 | 0.40 |
|  | d3 (mm) | 0.40 | 0.40 | 0.40 | 0.40 | 0.40 | 0.40 |
|  | L (mm) | 60.0 | 60.0 | 60.0 | 60.0 | 60.0 | 60.0 |
| STATE AFTER DURABILITY TEST | OCCURRENCE OF CRACKING | NOT IDENTIFIED | NOT IDENTIFIED | NOT IDENTIFIED | NOT IDENTIFIED | NOT IDENTIFIED | NOT IDENTIFIED |
|  | LEAKAGE CURRENT (μA) | 10 | 11 | 12 | 8 | 9 | 11 |
|  | DIFFUSION OF Pt | NOT IDENTIFIED | NOT IDENTIFIED | NOT IDENTIFIED | NOT IDENTIFIED | NOT IDENTIFIED | NOT IDENTIFIED |
|  | RESISTANCE INCREASE RATE (%) | 1.0 | 0.7 | 1.1 | 0.9 | 1.0 | 1.0 |

|  |  | EXAMPLE 7 | EXAMPLE 8 | EXAMPLE 9 | EXAMPLE 10 | EXAMPLE 11 |
|---|---|---|---|---|---|---|
| INSULATING LAYER | ALUMINA MATERIAL SPECIES | A | A | A | A | A |
|  | ADDITIVE RATE OF AIDS (wt %) | 6.0 | 6.0 | 6.0 | 0.1 | 10.0 |
|  | POROSITY (%) | 4.0 | 4.0 | 4.0 | 4.0 | 4.0 |
|  | THICKNESS t1 (μm) | 100 | 100 | 100 | 100 | 100 |
| HEATER LAYER | THICKNESS t2 (μm) | 30 | 30 | 30 | 30 | 30 |
| SIZE OF EACH COMPONENT OF SENSOR ELEMENT | d1 (mm) | 0.25 | 0.75 | 0.50 | 0.50 | 0.50 |
|  | d2 (mm) | 0.20 | 0.60 | 0.40 | 0.40 | 0.40 |
|  | d3 (mm) | 0.20 | 0.60 | 0.40 | 0.40 | 0.40 |
|  | L (mm) | 60.0 | 60.0 | 80.0 | 60.0 | 60.0 |
| STATE AFTER DURABILITY TEST | OCCURRENCE OF CRACKING | NOT IDENTIFIED | NOT IDENTIFIED | NOT IDENTIFIED | NOT IDENTIFIED | NOT IDENTIFIED |
|  | LEAKAGE CURRENT (μA) | 10 | 10 | 11 | 10 | 10 |
|  | DIFFUSION OF Pt | NOT IDENTIFIED | NOT IDENTIFIED | NOT IDENTIFIED | NOT IDENTIFIED | NOT IDENTIFIED |
|  | RESISTANCE INCREASE RATE (%) | 1.0 | 1.0 | 1.0 | 1.0 | 1.0 |

TABLE 2

| | | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 |
|---|---|---|---|---|---|---|
| INSULATING LAYER | ALUMINA MATERIAL SPECIES | B | B | A | A | A |
| | ADDITIVE RATE OF AIDS (wt %) | 6.0 | 6.0 | 6.0 | 6.0 | 6.0 |
| | POROSITY (%) | 35.1 | 5.0 | 4.0 | 4.0 | 4.0 |
| | THICKNESS t1 (μm) | 100 | 100 | 40 | 160 | 100 |
| HEATER LAYER | THICKNESS t2 (μm) | 30 | 30 | 30 | 30 | 5 |
| SIZE OF EACH COMPONENT OF SENSOR ELEMENT | d1 (mm) | 0.50 | 0.50 | 0.50 | 0.50 | 0.50 |
| | d2 (mm) | 0.40 | 0.40 | 0.40 | 0.40 | 0.40 |
| | d3 (mm) | 0.40 | 0.40 | 0.40 | 0.40 | 0.40 |
| | L (mm) | 60.0 | 60.0 | 60.0 | 60.0 | 60.0 |
| STATE AFTER DURABILITY TEST | OCCURRENCE OF CRACKING | NOT IDENTIFIED | NOT IDENTIFIED | NOT IDENTIFIED | IDENTIFIED | NOT IDENTIFIED |
| | LEAKAGE CURRENT (μA) | 10 | 11 | 105 | 8 | 10 |
| | DIFFUSION OF Pt | IDENTIFIED | IDENTIFIED | NOT IDENTIFIED | IDENTIFIED | NOT IDENTIFIED |
| | RESISTANCE INCREASE RATE (%) | 2.6 | 2.0 | 1.1 | 2.5 | 2.5 |

| | | COMPARATIVE EXAMPLE 6 | COMPARATIVE EXAMPLE 7 | COMPARATIVE EXAMPLE 8 | COMPARATIVE EXAMPLE 9 | COMPARATIVE EXAMPLE 10 |
|---|---|---|---|---|---|---|
| INSULATING LAYER | ALUMINA MATERIAL SPECIES | A | A | A | A | A |
| | ADDITIVE RATE OF AIDS (wt %) | 6.0 | 6.0 | 6.0 | 6.0 | 75.0 |
| | POROSITY (%) | 4.0 | 4.0 | 4.0 | 4.0 | 4.0 |
| | THICKNESS t1 (μm) | 100 | 100 | 100 | 100 | 100 |
| HEATER LAYER | THICKNESS t2 (μm) | 60 | 30 | 30 | 30 | 30 |
| SIZE OF EACH COMPONENT OF SENSOR ELEMENT | d1 (mm) | 0.50 | 0.20 | 0.80 | 0.50 | 0.50 |
| | d2 (mm) | 0.40 | 0.16 | 0.70 | 0.40 | 0.40 |
| | d3 (mm) | 0.40 | 0.16 | 0.70 | 0.40 | 0.40 |
| | L (mm) | 60.0 | 60.0 | 80.0 | 90.0 | 60.0 |
| STATE AFTER DURABILITY TEST | OCCURRENCE OF CRACKING | IDENTIFIED | IDENTIFIED | NOT IDENTIFIED | NOT IDENTIFIED | NOT IDENTIFIED |
| | LEAKAGE CURRENT (μA) | 10 | 11 | 76 | 85 | 86 |
| | DIFFUSION OF Pt | IDENTIFIED | IDENTIFIED | NOT IDENTIFIED | NOT IDENTIFIED | NOT IDENTIFIED |
| | RESISTANCE INCREASE RATE (%) | 2.6 | 2.4 | 1.0 | 1.1 | 1.0 |

Examples 1 to 11

The material species of alumina was set to the material species "A", and, regarding Example 1 as a reference, the porosity of the heater insulating layer 74 in Example 2 was set to have a value smaller than that in the other examples. The thickness t1 of the heater insulating layer 74 was set to be smaller in Example 3 than that in the other examples, and was set to be greater in Example 4 than that in the other examples. The thickness t2 of the heater element 72 was set to be smaller in Example 5 than that in the other examples, and was set to be greater in Example 6 than that in the other examples. The values of the end portion distance d1, the thickness direction distance d2, and the side portion distance d3 were set to be smaller in Example 7 than those in the other examples, and were set to be greater in Example 8 than those in the other examples. The value of the total length L of the sensor element 101 was set to be greater in Example 9 than that in the other examples. The amount of added aids was set to be smaller in Example 10 than that in the other examples, and was set to be greater in Example 11 than that in the other examples.

In each of the sensor elements 101 according to Examples 1 to 11, although the heater insulating layer 74 was formed as the densified layer having a porosity of 4.0% or 2.0% (only in Example 2), both the occurrence of cracking and diffusion of Pt in the heater insulating layer 74 were not identified after the durability test. The leakage current remained at 12 μA or less, and the resistance increase rate remained at 1.1% or less.

The results show that diffusion of Pt and the occurrence of cracking caused by the difference in coefficient of thermal expansion between the heater insulating layer 74 and the solid electrolyte layers (in particular, the second substrate layer 2 and the third substrate layer 3) are suitably prevented or reduced in the sensor element 101 in which the material species of alumina is the material species "A", the additive rate of the aids satisfies the range of 0.1 wt % to 10 wt %, the heater insulating layer is formed as the densified layer having a porosity of 4.0% or less, and all the above-mentioned sensor element dimensional conditions relating to the thickness t1 of the heater insulating layer 74, the thickness t2 of the heater element 72, the end portion distance d1, the thickness direction distance d2, the side portion distance d3, and the total length L of the sensor element 101 are satisfied.

In Example 2 in which the porosity of the heater insulating layer 74 was reduced to 2.0%, the resistance increase rate after the durability test was only 0.7%, which was the lowest in all Examples and Comparative Examples. This means that, in a case where the sensor element dimensional conditions are satisfied, it is preferable to set the porosity of the heater insulating layer 74 to 2.0% or less from the viewpoint of stability over time of the heater part 70 of the sensor element 101.

Comparative Examples 1 and 2

The sensor elements 101 according to Comparative Examples 1 and 2 were manufactured using the material species "B" as the material species of alumina. The other conditions to manufacture the sensor element 101 according to Comparative Example 1 were the same as those in Example 1. The sensor element 101 according to Comparative Example 2 was manufactured under the same conditions as those in Example 1 except that the firing conditions were adjusted so that the heater insulating layer 74 had a smaller porosity than that in Comparative Example 1.

In the sensor element 101 according to Comparative Example 1, the heater insulating layer 74 was formed as a porous layer having a porosity of 35.1%. On the other hand, in the sensor element 101 according to Comparative Example 2, the heater insulating layer 74 was formed as a relatively dense layer having a porosity of 5.0%.

The sensor elements 101 according to Comparative Examples 1 and 2 were similar to those according to Examples 1 to 11 in that the occurrence of cracking was not observed, and had a magnitude of the leakage current approximately equal to that in Examples 1 to 11, but diffusion of Pt was identified, and the resistance increase rate was 2.0% or more after the durability test.

The results show that diffusion of Pt is not prevented or reduced when the porosity of the heater insulating layer exceeds 4.0%.

Comparative Example 3

The sensor element 101 according to Comparative Example 3 was manufactured under the same conditions as those in Example 1 except that the thickness t1 of the heater insulating layer 74 was set to 40 µm, which was smaller than the lower limit (50 µm, corresponding to Example 3) in the sensor element dimensional conditions.

In the sensor element 101 according to Comparative Example 3, as in Examples 1 to 11, the heater insulating layer 74 was formed as the densified layer having a porosity of 4.0% or less, the occurrence of cracking was not observed, diffusion of Pt was not identified, and the resistance increase rate was only 1.1%, which approximately equal to that in the examples, but the leakage current had a value of 105 µA, which was significantly greater than that in Examples 1 to 11, after the durability test.

The results show that, in a case where the heater insulating layer 74 is provided as the densified layer to prevent or reduce cracking and diffusion of Pt in the sensor element 101, setting the value of the thickness of the heater insulating layer 74 to the value smaller than the lower limit in the sensor element dimensional conditions is not preferable because the heater insulating layer 74 does not produce an insulating effect, which is an original function, even though the effect of preventing or reducing cracking and diffusion of Pt can be obtained.

Comparative Example 4

The sensor element 101 according to Comparative Example 4 was manufactured under the same conditions as those in Example 1 except that the thickness t1 of the heater insulating layer 74 was set to 160 µm, which was greater than the upper limit (150 µm, corresponding to Example 4) in the sensor element dimensional conditions.

In the sensor element 101 according to Comparative Example 4, the heater insulating layer 74 was formed as the densified layer having a porosity of 4.0% or less, but both the occurrence of cracking and diffusion of Pt were identified, and the resistance increase rate exceeded 2.0% while the value of the leakage current was limited to 8 µA, which was approximately equal to that in Example 4, after the durability test.

The reason why cracking occurred in the sensor element 101 according to Comparative Example 4 is considered that the stress caused by the difference in coefficient of thermal expansion between the heater insulating layer 74 and the surrounding solid electrolyte layers (e.g., the second substrate layer 2 and the third substrate layer 3) was not sufficiently relaxed due to the thickness t1 of the heater insulating layer 74 greater than the upper limit in the sensor element dimensional conditions. The reason why Pt diffused despite the heater insulating layer 74 formed as the densified layer is considered that diffusion was caused through cracks as formed.

Comparative Example 5

The sensor element 101 according to Comparative Example 5 was manufactured under the same conditions as those in Example 1 except that the thickness t2 of the heater element 72 was set to 5 µm, which was smaller than the lower limit (10 µm, corresponding to Example 5) in the sensor element dimensional conditions.

In the sensor element 101 according to Comparative Example 5, as in Examples 1 to 11, the heater insulating layer 74 was formed as the densified layer having a porosity of 4.0% or less, the occurrence of cracking was not observed, diffusion of Pt was not identified, and the value of the leakage current was only 10 µA, which was approximately equal to that in the examples, but the resistance increase rate exceeded 2.0% after the durability test.

The fact that the resistance increased even though diffusion of Pt was not identified means that the increase in resistance was attributable to the heater element 72 itself. Since the sensor element 101 according to Comparative Example 5 was manufactured in a similar manner to that in Example 1 except that the thickness t2 of the heater element 72 was set to be smaller, it is determined that stability of the resistance value was impaired by setting the thickness t2 to have the smaller value.

The results show that setting the value of the thickness of the heater element 72 to the value smaller than the lower limit in the sensor element dimensional conditions is not preferable because the heater resistance value is not stabilized even though the effect of preventing or reducing cracking and diffusion of Pt can be obtained by providing the heater insulating layer 74 as the densified layer.

Comparative Example 6

The sensor element 101 according to Comparative Example 6 was manufactured under the same conditions as those in Example 1 except that the thickness t2 of the heater element 72 was set to 60 µm, which was greater than the upper limit (50 µm, corresponding to Example 6) in the sensor element dimensional conditions.

In the sensor element 101 according to Comparative Example 6, the heater insulating layer 74 was formed as the densified layer having a porosity of 4.0% or less, but both the occurrence of cracking and diffusion of Pt were identified, and the resistance increase rate exceeded 2.0% while the value of the leakage current was only 10 µA, which was approximately equal to that in Example 1, after the durability test.

The reason why cracking occurred in the sensor element 101 according to Comparative Example 6 is considered that the stress caused by the difference in coefficient of thermal expansion between the heater insulating layer 74 and the surrounding solid electrolyte layers (e.g., the second substrate layer 2 and the third substrate layer 3) was not sufficiently relaxed due to the thickness t2 of the heater element 72 greater than the upper limit in the sensor element dimensional conditions. The reason why Pt diffused despite the heater insulating layer 74 formed as the densified layer is considered that diffusion was caused through cracks as formed.

Comparative Example 7

The sensor element 101 according to Comparative Example 7 was manufactured under the same conditions as those in Example 1 except that the end portion distance d1, the thickness direction distance d2, and the side portion distance d3 were respectively set to 0.20 mm, 0.16 mm, and 0.16 mm, which were smaller than the respective lower limits (d1: 0.25 mm, d2: 0.20 mm, and d3: 0.20 mm, corresponding to Example 7) in the sensor element dimensional conditions.

In the sensor element 101 according to Comparative Example 7, the heater insulating layer 74 was formed as the densified layer having a porosity of 4.0% or less, but both the occurrence of cracking and diffusion of Pt were identified, and the resistance increase rate exceeded 2.0% while the value of the leakage current was only 11 µA, which was approximately equal to that in Example 1, after the durability test.

The reason why cracking occurred in the sensor element 101 according to Comparative Example 7 is considered that the stress caused by the difference in coefficient of thermal expansion between the heater insulating layer 74 and the surrounding solid electrolyte layers (e.g., the second substrate layer 2 and the third substrate layer 3) was not sufficiently relaxed due to the end portion distance d1, the thickness direction distance d2, and the side portion distance d3 smaller than the respective lower limits in the sensor element dimensional conditions. The reason why Pt diffused despite the heater insulating layer 74 formed as the densified layer is considered that diffusion was caused through cracks as formed.

Comparative Examples 8 and 9

The sensor element 101 according to Comparative Example 8 was manufactured under the same conditions as those in Example 1 except that the end portion distance d1, the thickness direction distance d2, and the side portion distance d3 were respectively set to 0.80 mm, 0.70 mm, and 0.70 mm, which were greater than the respective upper limits (d1: 0.75 mm, d2: 0.60 mm, and d3: 0.60 mm, corresponding to Example 8) in the sensor element dimensional conditions.

The sensor element 101 according to Comparative Example 9 was manufactured under the same conditions as those in Example 1 except that the value of the total length L of the sensor element 101 was set to 90.0 mm, which was greater than the upper limit (80.0 mm, corresponding to Example 9) in the sensor element dimensional conditions.

In each of the sensor elements 101 according to Comparative Examples 8 and 9, as in Examples 1 to 11, the heater insulating layer 74 was formed as the densified layer having a porosity of 4.0% or less, the occurrence of cracking was not observed, diffusion of Pt was not identified, and the resistance increase rate was only 1.0% or 1.1%, which was approximately equal to that in the examples, but the leakage current had a value (Comparative Example 8: 76 µA and Comparative Example 9: 85 µA) significantly greater than that in Examples 1 to 11 after the durability test. This is presumably because a large current was required when the sensor element 101 was heated due to large dimensions of the sensor element 101, leading to the increase in leakage current.

The results show that, in a case where the heater insulating layer 74 is provided as the densified layer to prevent or reduce cracking and diffusion of Pt in the sensor element 101, setting the values of the end portion distance, the thickness direction distance, the side portion distance, and the total length of the sensor element 101 to the values greater than the respective upper limits in the sensor element dimensional conditions is not preferable because the heater insulating layer 74 does not produce the insulating effect, which is the original function, even though the effect of preventing or reducing cracking and diffusion of Pt can be obtained.

The results in Comparative Examples 3 to 9 show that, in a case where the heater insulating layer 74 is provided as the densified layer to prevent or reduce cracking and diffusion of Pt in the sensor element 101, and the leakage current is prevented or reduced in the sensor element 101, the sensor element 101 is required to at least satisfy the sensor element dimensional conditions relating to the thickness t1 of the heater insulating layer 74, the thickness t2 of the heater element, the end portion distance d1, the thickness direction distance d2, the side portion distance d3, and the total length L of the sensor element 101.

Comparative Example 10

The sensor element 101 according to Comparative Example 10 was manufactured under the same conditions as those in Example 1 except that the amount of added aids when the insulating paste was manufactured was set to 15.0 wt %, which was greater than 10.0 wt % (corresponding to Example 11) as a maximum value in the other examples.

In the sensor element 101 according to Comparative Example 10, as in Examples 1 to 11, the heater insulating layer 74 was formed as the densified layer having a porosity of 4.0% or less, the occurrence of cracking was not observed, diffusion of Pt was not identified, and the resistance increase rate was only 1.0%, which was approximately equal to that in the examples, but the leakage current had a value of 86 µA, which was significantly greater than that in Examples 1 to 11, as in Comparative Example 3, after the durability test.

It is assumed that the reason why such a large leakage current was generated is, due to an excessive amount of added sintering aids when the insulating paste for heater insulating layer formation was manufactured, the sintering aids remaining in the heater insulating layer 74 which was formed using the insulating paste or a sub component derived from the remaining sintering aids formed a leakage path for the heater current.

It can thus be said that it is not preferable to add the excessive amount of sintering aids to the insulating paste for heater insulating layer formation when the heater insulating layer 74 is provided as the densified layer to prevent or reduce cracking and diffusion of Pt in the sensor element 101, because the leakage path is formed in the heater insulating layer 74, and the leakage path can cause the heater insulating layer 74 not to produce the insulating effect, which is the original function.

While the invention has been shown and described in detail, the foregoing description is in all aspects illustrative and not restrictive. It is therefore understood that numerous modifications and variations can be devised without departing from the scope of the invention.

What is claimed is:

1. A planar sensor element included in a gas sensor for detecting a predetermined gas component in a measurement gas, said sensor element comprising:
    a base part that is formed of an oxygen-ion conductive solid electrolyte; and
    a heater part that heats said sensor element, wherein said heater part includes:
        a heater element that generates heat by being externally powered, and contains Pt;
        an insulating layer that includes 90 wt % to 99.9 wt % of an insulating material having a different coefficient of thermal expansion from said solid electrolyte; and
        a heater electrode that is located on a main surface of said sensor element to be exposed, and is electrically connected to said heater element,
    a portion of said heater part other than said heater electrode is buried in said base part,
    said heater element is covered with said insulating layer,
    said insulating layer has a porosity of 4% or less,
    said insulating layer has a thickness of 50 μm to 150 μm,
    said heater element has a thickness of 10 μm to 50 μm,
    a thickness of the insulating layer is greater than a thickness of the heater element,
    a distance between an end portion of said sensor element and said insulating layer in a longitudinal direction of said sensor element is 0.25 mm to 0.75 mm,
    a distance between said main surface on which said heater electrode is located and said insulating layer in a direction of a thickness of said sensor element is 0.20 mm to 0.60 mm,
    a distance between a side surface of said sensor element and said insulating layer in a direction of a width of said sensor element is 0.20 mm to 0.60 mm, and
    a total length of said sensor element in said longitudinal direction is 80.0 mm or less.

2. The sensor element according to claim 1, wherein
    said oxygen-ion conductive solid electrolyte is zirconia, and
    said insulating material is α-alumina.

3. The sensor element according to claim 2, wherein said insulating layer has a porosity of 2% or less.

4. The sensor element according to claim 2, further comprising:
    a gas inlet that is located at one end portion of said base part;
    at least one internal space that is located inside said base part, and communicates with said gas inlet under a predetermined diffusion resistance; and
    at least one electrochemical pump cell that includes an outer pump electrode located on an outer surface of said base part, an inner pump electrode located to face said at least one internal space, and said solid electrolyte located between said outer pump electrode and said inner pump electrode, and pumps in and out oxygen between said at least one internal space and an outside, wherein
    said portion of said heater part other than said heater electrode is located, below a gas distribution part that extends from said gas inlet to said at least one internal space, along a direction in which said gas distribution part extends while being separated from said gas distribution part by said solid electrolyte.

5. The sensor element according to claim 1, wherein said insulating layer has a porosity of 2% or less.

6. The sensor element according to claim 5, further comprising:
    a gas inlet that is located at one end portion of said base part;
    at least one internal space that is located inside said base part, and communicates with said gas inlet under a predetermined diffusion resistance; and
    at least one electrochemical pump cell that includes an outer pump electrode located on an outer surface of said base part, an inner pump electrode located to face said at least one internal space, and said solid electrolyte located between said outer pump electrode and said inner pump electrode, and pumps in and out oxygen between said at least one internal space and an outside, wherein
    said portion of said heater part other than said heater electrode is located, below a gas distribution part that extends from said gas inlet to said at least one internal space, along a direction in which said gas distribution part extends while being separated from said gas distribution part by said solid electrolyte.

7. The sensor element according to claim 1, further comprising:
    a gas inlet that is located at one end portion of said base part;
    at least one internal space that is located inside said base part, and communicates with said gas inlet under a predetermined diffusion resistance; and
    at least one electrochemical pump cell that includes an outer pump electrode located on an outer surface of said base part, an inner pump electrode located to face said at least one internal space, and said solid electrolyte located between said outer pump electrode and said inner pump electrode, and pumps in and out oxygen between said at least one internal space and an outside, wherein
    said portion of said heater part other than said heater electrode is located, below a gas distribution part that extends from said gas inlet to said at least one internal space, along a direction in which said gas distribution part extends while being separated from said gas distribution part by said solid electrolyte.

* * * * *